United States Patent [19]

Uemura et al.

[11] Patent Number: 5,234,691
[45] Date of Patent: Aug. 10, 1993

[54] SUSTAINED-RELEASE PREPARARATION OF BASIC MEDICAL AGENT HYDROCHLORIDE

[75] Inventors: Akira Uemura, Ibaraki; Fumio Samizo, Moriguchi; Tetsuo Noguchi, Amagasaki, all of Japan

[73] Assignee: Sumitomo Pharmaceuticals Co., Ltd., Osaka, Japan

[21] Appl. No.: 603,484

[22] Filed: Oct. 26, 1990

[30] Foreign Application Priority Data

Oct. 27, 1989 [JP] Japan ................................ 1-280579

[51] Int. Cl.$^5$ .............................................. A61K 9/64
[52] U.S. Cl. ..................... 424/456; 424/464; 424/469; 424/480; 424/489; 424/495; 424/497
[58] Field of Search ............... 424/456, 480, 489, 495, 424/497

[56] References Cited

U.S. PATENT DOCUMENTS

| | | | |
|---|---|---|---|
| 3,458,622 | 7/1969 | Hill | 424/468 |
| 4,138,475 | 2/1979 | McAinsh et al. | 424/459 |
| 4,449,983 | 5/1984 | Cortese et al. | 609/892.1 |
| 4,777,033 | 10/1988 | Ikura et al. | 424/44 |
| 4,798,725 | 1/1989 | Patel | 424/456 |
| 4,904,649 | 2/1990 | Schwartz | 514/171 |

FOREIGN PATENT DOCUMENTS

| | | |
|---|---|---|
| 0322277 | 6/1989 | European Pat. Off. |
| 2148045 | 3/1973 | France |
| 3713092 | 6/1960 | Japan |
| 61-13683 | 4/1986 | Japan |
| 63-53966 | 10/1988 | Japan |
| 1334658 | 10/1973 | United Kingdom |
| 1468172 | 3/1977 | United Kingdom |
| 2017113 | 10/1979 | United Kingdom |
| 2025227 | 1/1980 | United Kingdom |
| 1568837 | 6/1980 | United Kingdom |
| 2075343 | 11/1981 | United Kingdom |

OTHER PUBLICATIONS

European Patent, Abstract, 322–277–A.
Japanese Patent, Abstract 2193–914–A.
European Patent Search 90 31 1748; Jun. 11, 1991; Amat A. Ventura, The Hague.
Patent Abstracts of Japan, vol. 14, No. 470, Oct. 15, 1990, p. 98 C 769 JPA 2193914.

*Primary Examiner*—Thurman K. Page
*Assistant Examiner*—Leon R. Horne
*Attorney, Agent, or Firm*—Sughrue, Mion, Zinn, Macpeak & Seas

[57] ABSTRACT

A preparation obtained by coating granules containing both a basic medical agent hydrochloride (e.g. allotinolol hydrochloride) and a polyanion the particles of which are present in the form of a discontinuous layer, with a film containing a slightly water-soluble substance, can release said agent at a controlled rate without influenced by the physiological factors of the gastrointestinal tract of a patient when orally administered.

14 Claims, 5 Drawing Sheets

SUSTAINED-RELEASE PREPARARATION OF BASIC MEDICAL AGENT HYDROCHLORIDE

BACKGROUND OF THE INVENTION

Field of the Invention

The present invention relates to a sustained-release preparation which, when orally administered, releases a basic medical agent at a controlled release rate without being influenced by the physiological factors of the gastrointestinal tract of a patient, and also relates to a method for preparing the sustained-release preparation.

Related Art Statement

In general, many of peroral drugs require to be administered one to three times per day, but for facilitating the compliance of a patient, it is considered desirable that only once administraction per day is effective enough. In such a case, the peroral drugs are usually prepared in the form of sustained-release preparations for maintaining their effective concentration in blood for a long period, and various techniques for such preparations have been reported.

For example, there have been reported a preparation in which the release rate of a drug is controlled by using a slightly water-soluble macromolecular substance or a wax together with the drug to form matrix [GB 2017113A], a preparation in which the release rate of a drug is controlled by coating an ordinary preparation such as granules, tablets or the like with films of a slightly water-soluble macromolecular substance or a wax [Japanese Patent Kokoku (Post-Exam Publn.) Nos. 61-13683 and U.S. Pat. No. 4138475], and an osmotic pressure pump device comprising a drug-holding portion and a portion capable of generating a pressure on contact with water, which are coated with a film of a slightly water-soluble macromolecular substance, the film having pores formed after the coating (U.S. Pat. No. 4449983).

As a technique which is a modification of techniques stated above, there is an attempt to control the dependence of drug release rate on pH value by adding a buffer and the like to granules, tablets or the like as cores, and coating the thus treated cores with films of a slightly water-soluble macromolecular substance [GB 1468172A, GB 2025227A, GB 2075343A; and Japanese Patent Kokoku (Post-Exam Publn.) No. 63-53966].

As the other techniques, some attempts have been reported to control the release rate of a medical agent from a preparation by utilizing the swelling of a polymer substance. For example, there may be exemplified a preparation prepared by mixing a medical agent with carboxyvinylpolymer or polyvinylpyrrolidone followed by capsulation or by compression to prepare a tablet (U.S. Pat. Nos. 4,798,725 and 3,458,622), or by coating with film after tabletting (G.B. 1,568,837).

Of the conventional techniques, the osmotic pressure pump device is a widely applicable technology but its production requires a very complicated process. Moreover, the following possibility has been pointed out. Since the osmotic pressure pump device usually has a single-unit dosage form, the bioavailability of an active agent is varied by the difference of the enterokinesis of a patient, in particular, the difference of gastric emptying rate, or a preparation stagnates at one place of the gastrointestinal tract, so that the local concentration of a drug is increased, resulting in adverse side effects caused in the mucosa of the gastrointestinal tract [A. H. Beckett, The Pharmaceutical Journal, Vol. 231, p. 232 (1983)].

Matrix type sustained-release preparations, coating type sustained-release preparations, or preparations having a controlled drug release rate independent of pH value by virtue of the addition of a buffer and the like to granules, tablets or the like as cores, are easily producible and commercially advantageous. However, when such techniques are applied to hydrochlorides of basic medical agents, it is often observed that the release of the agents varies depending on the composition and fluidity of the liquid in release environment.

This is because the solubility of the basic medical agent hydrochloride varies depending not only on pH value but also on the concentration of chloride ion present together with them. This fact indicates that when a preparation is administered to a patient, the agent concentration in blood varies, namely, the bioavailability varies, owing to the variation of the release rate of the agent which is dependent on the physiological factors of the gastrointestinal tract, in particular, the amount and fluidity of the digestive juice or the amount and quality of meals.

In the case of sustained-release preparations, the dose is usually larger than that in the case of ordinary rapidly soluble preparations, and hence the variation of the bioavailability is very dangerous to a patient. Therefore, it is eagerly desirable to develop a sustained-release preparation in which the release of a basic medical agent is not affected by the composition and fluidity of the liquid in release environment.

SUMMARY OF THE INVENTION

In order to solve such problems, the present inventors have conducted various researches on the dissolution behaviors of basic agent hydrochlorides and preparations containing them, and consequently have found that by coating granules containing both a basic agent hydrochloride and a polyanion the particles of which are present in the form of a discontinuous layer with a film containing a slightly water-soluble substance, the release speed of the agent can be controlled, whereby the present invention has been accomplished.

That is, the present invention relates to a sustained-release preparation characterized in that its sustained-release function is formed by coating granules containing both a basic medical agent hydrochloride and a polyanion the particles of which are present in the form of a discontinuous layer, with a film containing a slightly water-soluble substance.

The present invention also relates to a method for preparing the sustained-release preparation, which comprises the steps of:

mixing and kneading a basic medical agent hydrochloride with a polyanion to form granules under the condition that the polyanion is not completely dissolved; and coating said granules with a film containing a slightly water-soluble substance.

The sustained-release preparation of the present invention may be applicable to various drugs. For example, it may be applicable to various drugs such as depressors, vitamin compounds, anti-inflammatory agents, drugs for arteriosclerosis, hormone preparations, immunomodulators and anti-infectives.

DETAILED DESCRIPTION OF THE INVENTION

The agent used in the sustained-release preparation of the present invention may be either solid or liquid, so long as it is a basic medical agent and is dissociated and dissolved to exhibit some therapeutic effect in the liquid in gastrointestinal tract when orally administratered. When it is solid, it may be used in the form of fine powders as obtained by pulverization.

The polyanion used in the sustained-release preparation of the present invention is a substance wherein a functional group which is dissociated in water to obtain a negative charge is present in the side chain of the polymer chain. Typical examples of the substance are polymers having a carboxyl group in the side chain.

As said substance, there may be exemplified polyglutamic acids, maleic acid-divinyl ether copolymers, hydroxypropylmethyl cellulose phthalates, hydroxypropylmethyl cellulose acetate succinates, cellulose acetate phthalates, carboxymethylethyl celluloses, methacrylic acid copolymers, alginic acids, carboxyvinyl polymers, carboxymethyl celluloses, salts thereof, and mixtures of these compounds. More preferably, there may be exemplified carboxyvinyl polymers, carboxymethyl celluloses, salts thereof, and mixtures of these compounds. The salts include, for example, calcium salts and sodium salts. The above substances become polyanions when the carboxyl group present in the molecule is dissociated.

The slightly water-soluble substance used in the sustained-release preparation of the present invention is not critical so long as it has a very low solubility in water and forms a coating film at ordinary temperature by its intermolecular force. As such a slightly water-soluble substance, slightly water-soluble macromolecular substances or waxes may be exemplified. The slightly water-soluble substance includes, for example, polyvinyl acetates, ethyl celluloses, hydroxypropylmethyl cellulose acetate succinates, aminoalkylmethacrylate copolymers, methacrylic acid copolymers, cellulose acetates, polyethylenes, polymethyl methacrylates, polydimethylsiloxanes, hardened oil, beeswax, carnauba wax, sucrose fatty acid esters, sorbitan monostearate, glyceryl monostearate, glyceryl monomyristate, glyceryl distearate, stearic acid, stearyl alcohol, and mixtures thereof. More preferable examples of the slightly water-soluble substance are ethyl celluloses, hydroxypropylmethyl cellulose acetate succinates, aminoalkyl methacrylate copolymers, methacrylic acid copolymers, and mixtures thereof.

Next, the mechanism of the sustained-release preparation of the present invention is explained below.

It may be considered that in general, the release of a drug from granules having a coating film outside is affected by (1) the existence or formation of flow paths by which a liquid and the drug flow, (2) the diffusion rates of the drug in the granules and in the liquid in release environment, and (3) the solubility of the drug in the liquid in release environment. The solubility and the diffusion rate of the drug in the liquid in release environment are unequivocally determined and hence uncontrollable, but the other factors may be considered controllable.

Accordingly, in the sustained-release preparation of the present invention, granules containing, besides a basic medical agent hydrochloride, a polyanion the particles of which are present in the form of a discontinuous layer are used in order to limit the existence or formation of flow paths by which the liquid in release environment and the drug flow and to limit the diffusion rate of the drug in the granules. The effect of the polyanion may be explained as follows.

In general, a polyanion is dissociated and dissolved or swollen in a neutral liquid having a low ionic strength. Therefore also, when contained in granules, it undergoes the same change as described above, in the case where the liquid in release environment which invades from the outside of a coating layer is a neutral liquid having a low ionic strength. When dissolved, the polyanion increases the viscosity of the liquid, which is characteristic of a macromolecular substance, and hence it limits the diffusion rate of a drug in the granules. When the polyanion is swollen, spaces which are present at early stage are filled with the swollen polymer, resulting in restriction of the formation of flow paths through which the liquid in release environment flows.

On the other hand, when the liquid in release environment is acidic owing to the existence of hydrochloric acid, the polyanion is not dissolved or swollen and hence does not exert the actions as described above.

What is important here is that the particles of the polyanion are present in the form of a discontinuous layer. If they are present in the form of a continuous layer in contrast to the present invention, in the case where the liquid in release environment is acidic owing to the existence of hydrochloric acid, the whole granules containing the drug are not dissolved or swollen, so that the liquid in release environment does not invade the granules at all, and therefore the drug is not released at all. However, in the present invention, the particles of the polyanion are present in the form of a discontinuous layer, so that also when the liquid in release environment is acidic owing to the existence of hydrochloric acid, the liquid invade the granules in an amount sufficient for dissolution of the drug.

On the other hand, the solubility of the basic medical agent hydrochloride is lower in a solution which is acidic owing to the existence of hydrochloric acid, because of the common-ion effect than in a neutral liquid having a low ionic strength. That is, normal gastric juice is acidic owing to the existence of hydrochloric acid under physiologically conceivable conditions, so that the solubility of the basic medical agent hydrochloride in the gastric juice is low, while the gastric juice of the stomach of a patient with achlorhydria is a neutral liquid having a low ionic strength, so that the solubility of the basic medical agent hydrochloride is high.

That is, in a neutral liquid having a low ionic strength in which the solubility of the basic medical agent hydrochloride is high, the release rate of the agent is determined by the effect of the polyanion. On the other hand, in a solution which is acidic owing to the existence of hydrochloric acid, the release rate of the agent is determined by the solubility of the basic agent hydrochloride.

Furthermore, in the sustained-release preparation of the present invention, the granules are coated with a film former containing a slightly water-soluble substance in order to limit paths for the liquid and the drug into the coating film, and the release rate of the agent can be properly controlled by changing the composition or thickness of the coating film.

By virtue of such effects, the release of the agent from the preparation is substantially constant even when there varies the composition and fluidity of a liquid in release environment. In other words, the release of the agent from the preparation is not influenced by the physiological factors in the gastrointestinal tract of a patient. This means that the release of the agent from the preparation is not different even when the gastric juice secretion of a patient is excessive, or even when it is not sufficient, or even when a large amount of water or food is taken. Such a characteristic is very useful in practice.

In the sustained-release preparation of the present invention, pharmaceutically acceptable additives may be used in addition to the components as described above. The pharmaceutically acceptable additives include additives which are essential in view of formulation technique, such as excipients, disintegrators, binders, lubricants and coating agents; additives as used in a slight amount for enhancing the commercial value of the preparation, such as coloring agents and flavoring agents; and drugs other than the basic medical agent hydrochloride contained in the coated granules.

All of these pharmaceutically acceptable additives are not critical and those generally used in solid preparations may be used.

Such additives may be used also as either constituents of the granules as cores, or constituents of the coating film outside the granules. In addition, when hard capsules or tablets are prepared as one embodiment of the present invention, such additives may be made into particles of pharmaceutically acceptable additives or a particulate matter comprising pharmaceutically acceptable additives, mixed with the coated granules containing the basic medical agent hydrochloride, and then packed into hard gelatin capsules or pressed into tablets.

Furthermore, like the above-mentioned pharmaceutically acceptable additives, the same drug as the basic medical agent hydrochloride contained in the coated granules can be added as a rapidly soluble component to a portion in the preparation other than the coated granules.

In the sustained-release preparation of the present invention, there may be employed various combinations of the proportions of constituents of the core of the coated granule with the proportions of constituents of the coating film. The effect of the present invention can be expected, for example, by employing the following composition: the medical agent hydrochloride and the polyanion are 99 w/w% or less and 1-70 w/w%, respectively, based on the weight of the granule as core; the slightly water-soluble substance is 40 w/w% or more based on the weight of the coating film. A preferable combination is as follows: the medical agent hydrochloride and the polyanion are 70% or less and 1-60%, respectively, based on the weight of the granule as core; the slightly water-soluble substance is 50% or more based on the weight of the coating film. A particularly preferably combination is as follows: the medical agent hydrochloride and the polyanion are 50% or less and 2-50%, respectively, based on the weight of the granule as core; the slightly water-soluble substance is 60% or more based on the weight of the coating film. The above proportions are those of the components only in the coated granules of a preparation, and components of the preparation other than the coated granule are not included in the above proportions. The ratio of the total coated granules to the total of components of the preparation other than the coated granules is not critical because it does not participate in the control of release rate of the medical agent.

A method for preparing a preparation wherein the above-mentioned coated granules, i.e., the granules containing both the basic medical agent hydrochloride and the polyanion the particles of which are present in the form of a discontinuous layer are coated with the film containing the slightly water-soluble substance, is not critical. Said preparation may be obtained by various methods which are well known as techniques for preparing pharmaceuticals.

First, for preparing the granules as cores, there may be employed a wet granulation method, dry granulation method, fluidized-bed granulation method and melt granulation method. The most useful method is extrusion granulation method belonging to the wet granulation method. In the case of the extrusion granulation method, the basic medical agent hydrochloride, the polyanion and if necessary, other constituents are mixed, thereafter kneaded together by the use of water or an organic solvent, and then subjected to extrusion granulation. In this case, there may be used a kneading liquid as prepared by dissolving or dispersing a well-known binder in water or an organic solvent. The granules as cores may be obtained by forming the granules obtained by the extrusion granulation into a spherical shape or shifting them to make the particle size uniform, and then conducting drying, or by shifting them to make the particle size uniform, after drying. Here, the constituents of the granules as cores other than the polyanion may be used in the form of powder or a kneading liquid as obtained by dissolving or suspending them in organic solvent.

In the present invention, the particles of the polyanions should be present in the granules in the form of a discontinuous layer, and therefore the polyanion is used usually in powder form. Depending on circumstances, it may be used also in suspension form by the use of a solvent in which the polyanion is not completely soluble. In either case, in a usual kneaded state, i.e., a state in which the solid component is wetted with a liquid component, the polyanion particles are present in the form of a discontinuous layer and does not form a continuous layer on subsequent granulation and drying. For preparating the granules as cores, there may also be employed a wet granulation method, a dry granulation method, a fluidized-bed granulation method and a melt granulation method. When any of these methods is employed, the polyanion particles can be allowed to exist in the form of a discontinuous layer preferably by using the polyanion in the form of power or by using a suspension in a solvent in which the polyanion is not completely soluble.

Next, as a method for coating the granules as cores with a film containing a slightly water-soluble substance, there may be employed a pan coating method, a fluidized-bed coating method and a centrifugal flow coating method. In all of these methods, on a layer in which the granules as cores are being rolled or allowed to flow, the coating agent containing the slightly water-soluble substance is sprayed in the form of a coating liquid obtained by dissolving or dispersing the coating agent in water or an organic solvent, and the water or the organic solvent is allowed to evaporate in warm air, whereby coating films are formed outside the granules as cores. These methods are per se well known and the sustained-release preparation of the present invention may be prepared by any of them.

Thus, the coated granule is formed. A portion in the preparation which participates in the control of the dissolution rate of the sustained-release preparation is the coated granule portion. The coated granules may be used as a granular preparation as they are. It is also possible to obtain the sustained-release preparation of the present invention by formulating the coated granules into any of various solid preparations such as hard capsules and tablets by a heretofore well-known formulation procedure such as packing into capsules or tableting.

In such preparations, a plurality of the coated granules are dispersed in one piece of the preparation. When administered in practice, the preparation is disintegrated to release the basic medical agent sustainedly from the individual coated granules.

As explained above in detail, in the sustained-release preparation of a basic medical agent hydrochloride of the present invention, the release of the basic medical agent is controlled by taking advantage of not only characteristics of the basic medical agent hydrochloride but also the effects of the polyanion and the slightly water-soluble substance in the coated granules portion contained in said preparation. Accordingly, the release of the basic medical agent is not easily affected by the composition, fluidity and the like of the liquid in release environment, and when the preparation is administered to a patient, the release rate of the agent does not varies depending on the physiological factors of the gastrointestinal tract, in particular, the amount and fluidity of the digestive juice or the amount and quality of meals, so that the variation of concentration of the medical agent in blood can be minimized.

Therefore, the present invention has made it possible to provide a useful sustained-release preparation having an improved bioavailability, in the case of a basic agent hydrochloride.

The present invention is specifically illustrated with reference to the following comparative examples and examples of the present invention, which should not be construed as limiting the scope of the invention.

COMPARATIVE EXAMPLE 1

For comparison with the sustained-release preparation of the present invention, there was prepared an arotinolol hydrochloride [chemical name: 5-{2-[(3-tert-butylamino-2-hydroxypropyl) thio]-4-thiazolyl}-2-thiophenecarboxamide hydrochloride] prolonged-action preparation using a matrix solid composed of a slightly water-soluble substance and an excipient, which is a heretofore well-known technique.

| [Recipe] | |
|---|---|
| Arotinolol hydrochloride | 20 g |
| Corn starch | 90 g |
| Polyvinyl acetate | 90 g |
| Total | 200 g |

According to the above recipe, arotinolol hydrochloride and corn starch were mixed in a stirring type mixer for 10 minutes, and then a polyvinyl acetate solution was added, followed by kneading for 5 minutes. Thereafter, the kneaded product was passed through a No. 12 sieve to obtain a particulate matter, which was then dried to obtain a matrix solid particulate matter. The polyvinyl acetate was used for kneading in the form of a 30 w/w% solution of the polyvinyl acetate in a mixed solvent of 50 w/w% of ethanol and 50 w/w% of dichloromethane.

In the thus obtained preparation, arotinolol hydrochloride and corn starch were coated with the polyvinyl acetate which is not a polyanion and which forms a continuous layer, and the preparation is therefore different from the preparation of the present invention.

Figure 1:
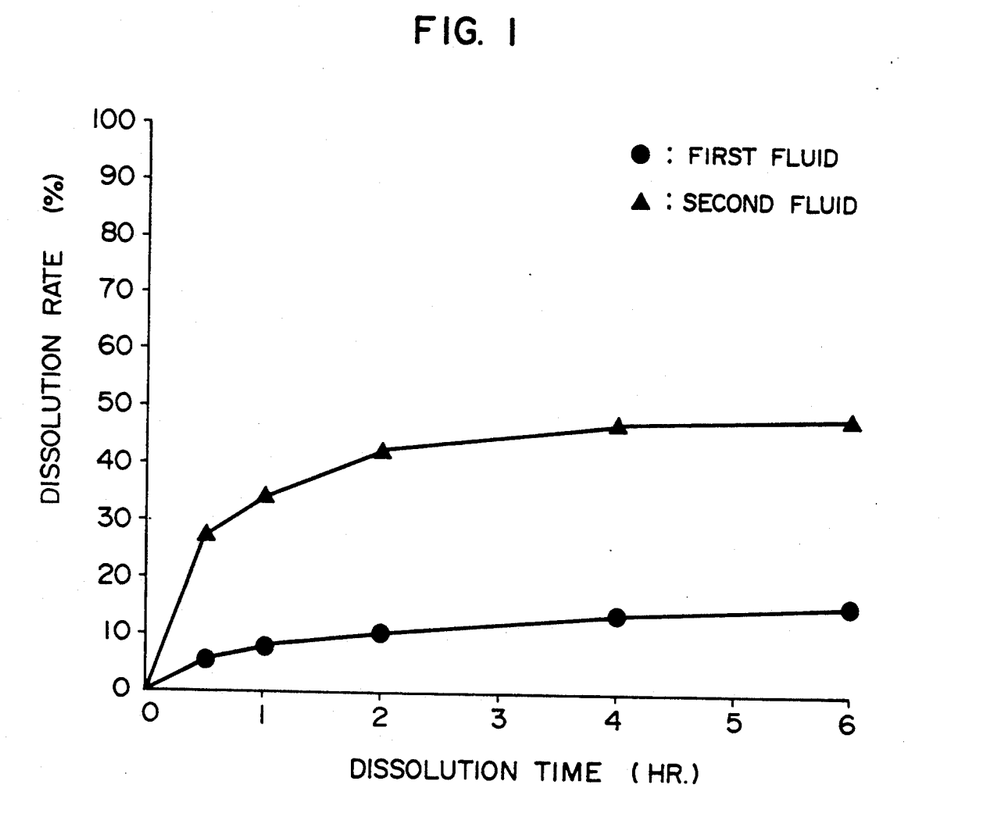
FIG. 1 shows the results of the dissolution test in Comparative Example 1.

In accordance with the second method (the paddle method) in the dissolution test methods prescribed in the 11th revised Japanese Pharmacopoeia, the dissolution test for arotinolol hydrochloride was carried out on the matrix solid particulate matter to give the results shown in FIG. 1. In the present comparative example, there was observed a large difference between the dissolution rate in the first fluid and the second fluid in the disintegration test method prescribed in the 11th revised Japanese Pharmacopoeia.

The first fluid in the disintegration method prescribed in the 11th revised Japanese Pharmacopoeia is 900 ml of an aqueous solution with pH of about 1.2 containing hydrochloric acid and sodium chloride, and the second solution in the disintegration method prescribed in the 11th revised Japanese Pharmacopoeia is 900 ml of an aqueous solution with a pH of about 6.8 containing monobasic potassium phosphate and sodium hydroxide. The revolution rate of paddle is 100 r.p.m.

Therefore, the results shown in FIG. 1 indicate that the release of arotinolol hydrochloride from the sustained-release preparation of the present comparative example is greatly affected by the composition, fluidity and the like of the liquid in release environment.

COMPARATIVE EXAMPLE 2

For comparison with the sustained-release preparation of the present invention, there was prepared an arotinolol hydrochloride sustained-release preparation consisting of allotinolol-hydrochloride-containing granules coated with a film former containing a slightly water-soluble substance, which is a heretofore well-known technology.

| [Recipe for granules] | |
|---|---|
| Arotinolol hydrochloride | 400 g |
| Crystalline cellulose | 100 g |
| Hydroxypropyl cellulose | 100 g |
| Lactose | 270 g |
| Polyvinyl alcohol | 30 g |
| Total | 900 g |

According to the above recipe, the four ingredients from arotinolol hydrochloride to lactose were mixed in a stirring type mixer for 10 minutes, and 300 g of a 10 w/w% aqueous polyvinyl alcohol solution was added, followed by kneading for 5 minutes. The kneaded product was subjected to extrusion granulation by means of a granulator having a screen with a diameter of 0.8 mm, formed into a spherical shape by a conventional method, and then dried in a fluidized-bed dryer, whereby granules as cores were prepared.

| [Recipe for a coating liquid] | |
| --- | --- |
| Ethyl cellulose | 90 g |
| Hydroxypropylmethyl cellulose | 10 g |
| Ethanol | 450 g |
| Methylene chloride | 450 g |
| Total 100 g as solid | |

300 Grams of the granules as cores were coated with the above coating liquid by means of a fluidized-bed coating apparatus to obtain sustained-release granules.

In the thus obtained preparation, the granules did not contain a polyanion, and the preparation is therefore different from the preparation of the present invention.

Figure 2:
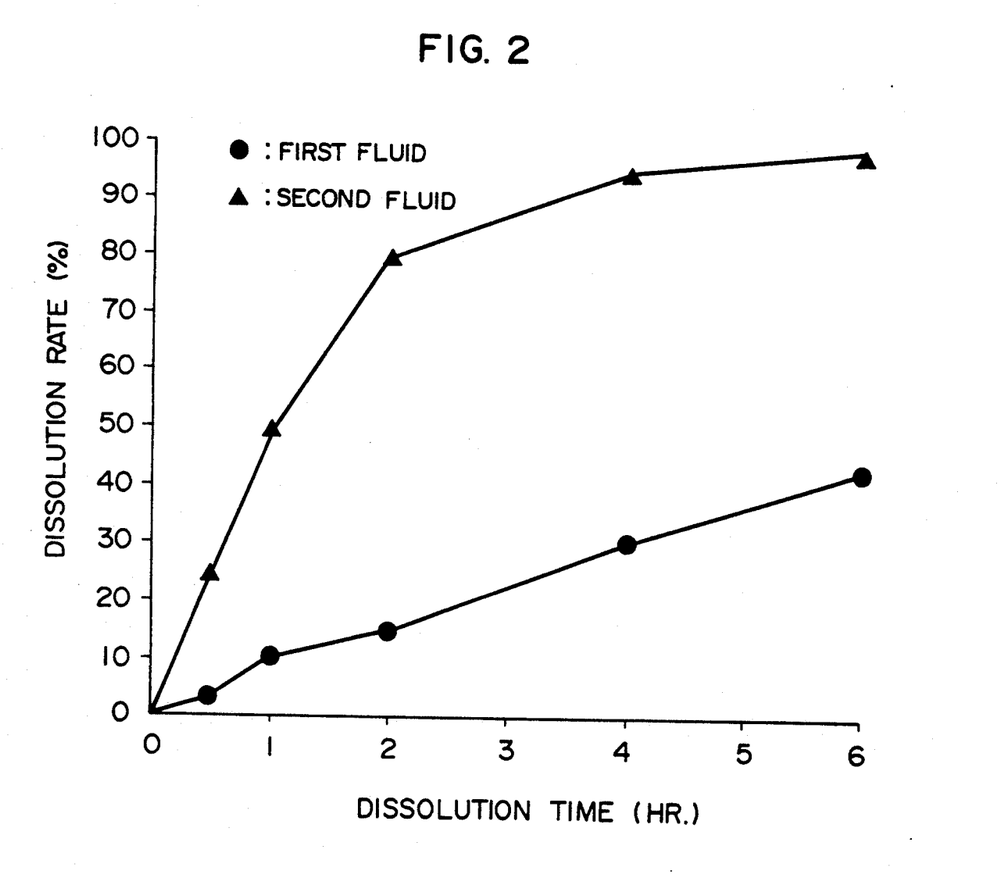
FIG. 2 shows the results of the dissolution test in Comparative Example 2.

The dissolution test for arotinolol hydrochloride was carried out on the sustained-release granules in the same way as in Comparative Example 1 to give the results shown in FIG. 2. In the present comparative example, there was observed a large difference between the dissolution rate in the first fluid and the second solution in the disintegration test method prescribed in the 11th revised Japanese Pharmacopoeia.

Therefore, the results shown in FIG. 2 indicate that the release of arotinolol hydrochloride from the sustained-release preparation of the present comparative example is greatly affected by the composition, fluidity and the like of the liquid in release environment.

EXAMPLE 1

The sustained-release preparation of the present invention was prepared in the following manner by using arotinolol hydrochloride.

| [Recipe for granules] | |
| --- | --- |
| Arotinolol hydrochloride | 200 g |
| Carboxymethyl cellulose calcium | 200 g |
| Polyvinyl alcohol | 24 g |
| Total | 424 g |

According to the above recipe, arotinolol hydrochloride and carboxymethyl cellulose calcium were mixed in a stirring type mixer for 10 minutes, and then 240 g of a 10 w/w% aqueous polyvinyl alcohol solution was added, followed by kneading for 5 minutes. The kneaded product was subjected to extrusion granulation by means of a granulator having a screen with a diameter of 0.8 mm, dried in a fluidized-bed dryer, and then shifted to make the particle size uniform, whereby granules as cores were prepared.

| [Recipe for a coating liquid] | |
| --- | --- |
| Ethyl cellulose | 90 g |
| Hydroxypropylmethyl cellulose | 10 g |
| Ethanol | 450 g |
| Methylene chloride | 450 g |
| Total 100 g as solid | |

400 Grams of the granules as cores were coated with the above coating liquid by means of a fluidized-bed coating apparatus to obtain sustained-release granules.

Figure 3:
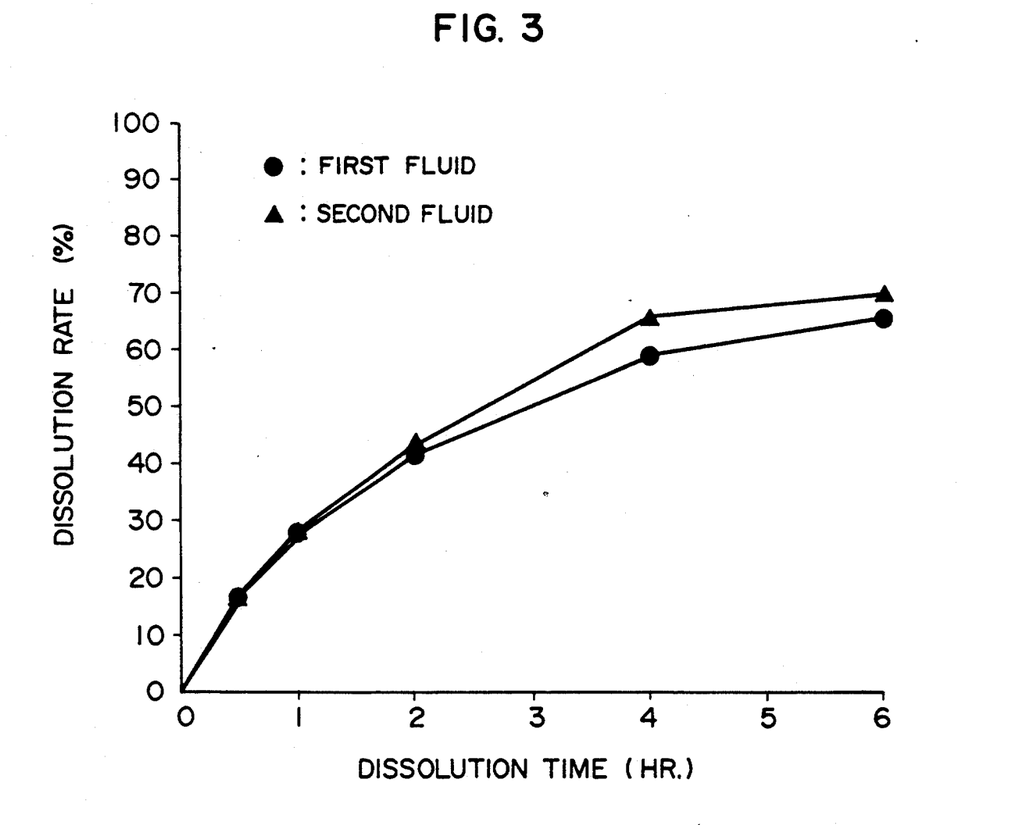
FIG. 3 shows the results of the dissolution test in Example 1.

The dissolution test for arotinolol hydrochloride was carried out on the sustained-release granules in the same way as in Comparative Example 1 to give the results shown in FIG. 3. In the present example, there was observed little difference between the dissolution rates in the first fluid and the second fluid in the disintegration test method prescribed in the 11th revised Japanese Pharmacopoeia.

Therefore, the results shown in FIG. 3 indicate that the release of arotinolol hydrochloride from the sustained-release preparation of the present example is not affected by the composition, fluidity and the like of the liquid in release environment.

EXAMPLE 2

The sustained-release preparation of the present invention was prepared in the following manner by using arotinolol hydrochloride.

| [Recipe for granules] | |
| --- | --- |
| Arotinolol hydrochloride | 170 g |
| Crystalline cellulose | 320 g |
| Hydroxypropyl cellulose | 40 g |
| Carboxyvinyl polymer | 46 g |
| Lactose | 224 g |
| Total | 800 g |

According to the above recipe, the five ingredients from arotinolol hydrochloride to lactose were mixed in a stirring type mixer for 10 minutes, and then 300 g of deionized water was added, followed by kneading for 5 minutes. The kneaded product was subjected to extrusion granulation by means of a granulator having a screen with a diameter of 0.7 mm, formed into a spherical shape by a conventional method, and then dried in a fluidized-bed dryer, whereby granules as cores were prepared.

| [Recipe for a coating liquid] | |
| --- | --- |
| Ethyl cellulose | 105 g |
| Hydroxypropylmethyl cellulose | 45 g |
| Ethanol | 1350 g |
| Methylene chloride | 675 g |
| Total 150 g as solid | |

400 Grams of the granules as cores were coated with the above coating liquid by means of a fluidized-bed coating apparatus to obtain sustained-release granules.

Figure 4:
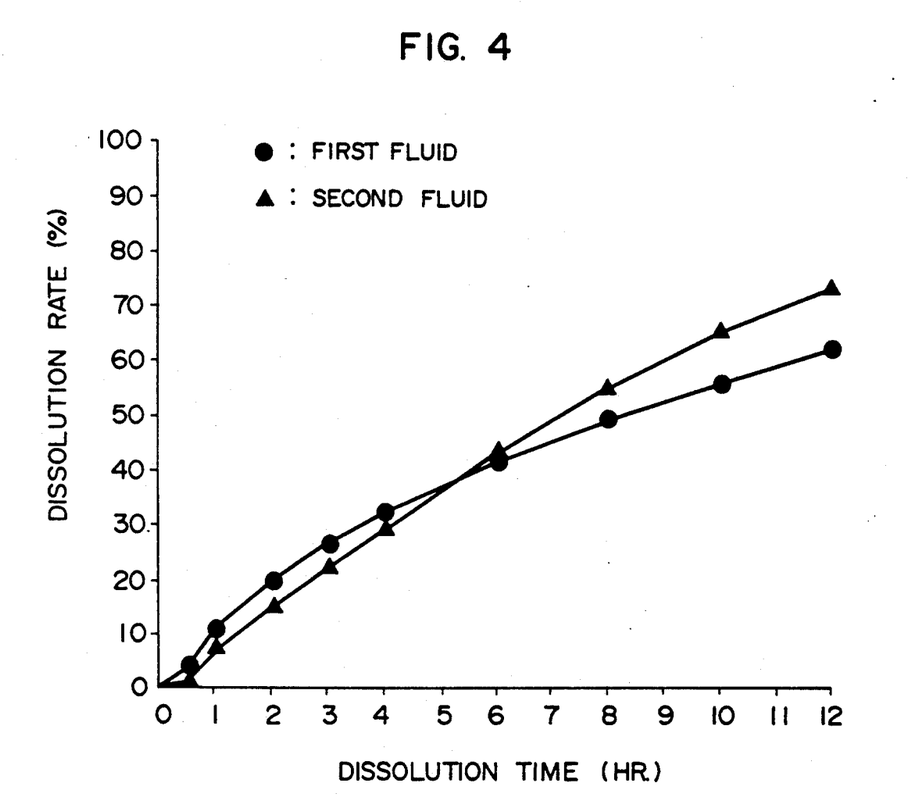
FIG. 4 shows the results of the dissolution test in Example 2.

The dissolution test for arotinolol hydrochloride was carried out on the sustained-release granules in the same way as in Comparative Example 1 to give the results shown in FIG. 4. In the present example, there was observed little difference between the release rates in the first fluid and the second fluid in the disintegration test method prescribed in the 11th revised Japanese Pharmacopoeia.

Therefore, the results shown in FIG. 4 indicate that the release of arotinolol hydrochloride from the sustained-release preparation of the present example is not affected by the composition, fluidity and the like of the liquid in release environment.

EXAMPLE 3

The sustained-release preparation of the present invention was prepared in the following manner by using the arotinolol hydrochloride sustained-release preparation of Example 2.

| [Recipe for rapidly soluble granules] | |
| --- | --- |
| Arotinolol hydrochloride | 50 g |
| Crystalline cellulose | 680 g |
| Carboxymethyl cellulose calcium | 100 g |
| Lactose | 330 g |
| Polyvinyl alcohol | 40 g |
| Total | 1200 g |

Rapidly soluble granules were prepared according to the above recipe by conventional wet crushing granulation. 240 Grams of these granules, 160 g of the sustained-release granules prepared in Example 2, and 0.8 g of magnesium stearate were mixed. Using the resulting mixture, tablets of 8 mm in diameter each having a weight of about 200 mg were prepared by means of a rotary tableting machine.

Figure 5:
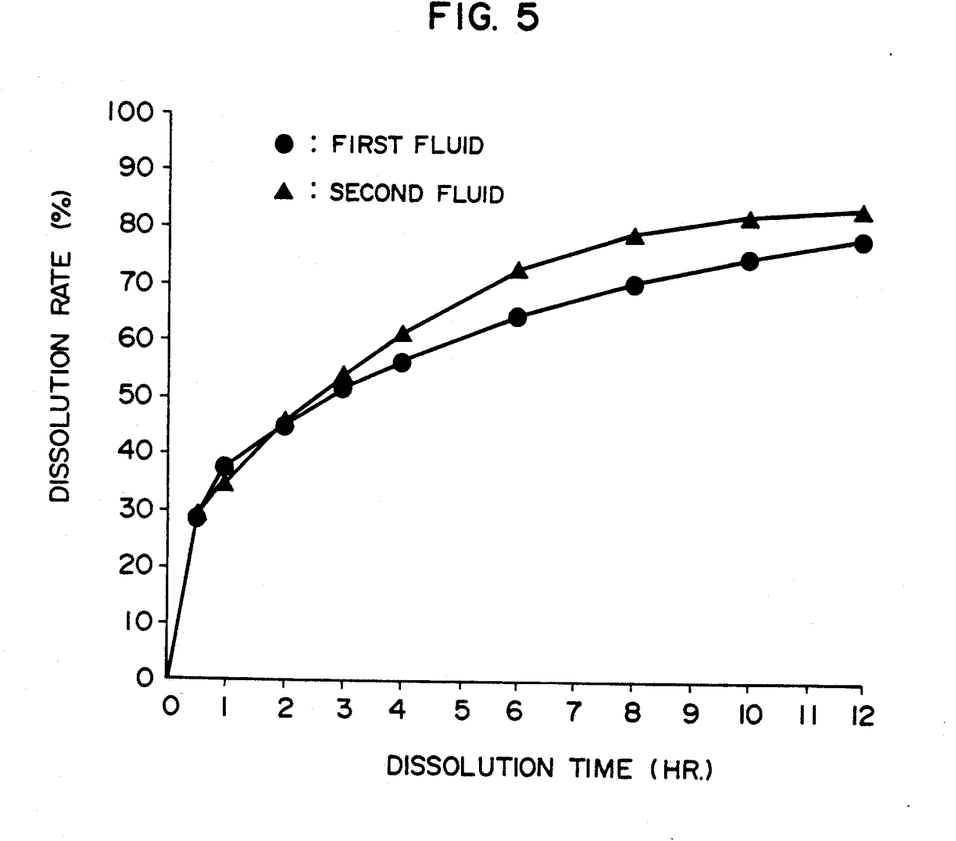
FIG. 5 shows the results of the dissolution test in Example 3.

The dissolution test for arotinolol hydrochloride was carried out on the thus obtained sustained-release tablets containing the rapidly soluble portion in the same way as in Comparative Example 1 to give the results shown in FIG. 5. In the present example, there was observed little difference between the release rates in the first fluid and the second fluid in the disintegration test method prescribed in the 11th revised Japanese Pharmacopoeia.

Therefore, the results shown in FIG. 5 indicate that the release of arotinolol hydrochloride from the sustained-release preparation of the present example is not affected by the composition, fluidity and the like of the liquid in release environment.

What we claim is:

1. A sustained-release preparation comprising granules containing both a basic medical agent hydrochloride and a polyanion having a carboxy group in the side chain the particles of which are present in the form of a discontinuous layer, said polyanion being selected from the group consisting of carboxyvinyl polymers, carboxymethyl celluloses, salts thereof and mixtures of these compounds, said granules being coated with a film containing a slightly water-soluble macromolecular substance selected from polyvinyl acetates, ethyl celluloses, aminoalkylmethacrylate copolymers, methacrylic acid copolymers, cellulose acetates, polyethylenes, polymethyl methacrylates, polydimethyl-siloxanes, hardened oil, beeswax, carnauba wax, sucrose fatty acid esters, sorbitan monostearate, glyceryl monostearate, glyceryl monomyristate, glyceryl distearate, stearic acid, stearyl alcohol, and mixtures thereof.

2. A sustained-release preparation according to claim 1, wherein arotinolol hydrochloride is used as the basic medical agent hydrochloride.

3. A sustained-release preparation according to claim 1, wherein the slightly water-soluble substance is an ethyl cellulose, a hydroxypropylmethyl cellulose acetate succinate, an aminoalkylmethacrylate copolymer, a methacrylic acid copolymer, or a mixture thereof.

4. A sustained-release preparation according to claim 1, 2, or 3, wherein particles of at least one pharmaceutically acceptable additive or a particulate matter comprising at least one pharmaceutically acceptable additive is packed into hard gelatin capsules or tableted together with the coated granules.

5. A sustained-release preparation according to claim 1, 2, or 3, wherein particles of at least one pharmaceutically acceptable additive or a particulate matter comprising at least one pharmaceutically acceptable additive, which contains a basic medical agent hydrochloride, is packed into hard gelatin capsules or tableted together with the coated granules which contains the same basic medical agent hydrochloride.

6. A method for preparing the sustained-release preparation according to claim 1, which comprises the steps of:
   mixing and kneading a basic medical agent hydrochloride with a polyanion having a carboxy group in the side chain to form granules under the condition that the polyanion is not completely dissolved, said polyanion being selected from the group consisting of carboxyvinyl polymers, carboxymethyl celluloses, salts thereof, and mixtures of these compounds; and
   coating said granules with a film containing a slightly water-soluble macromolecular substance selected from polyvinyl acetates, ethyl celluloses, aminoalkylmethacrylate copolymers, methacrylic acid copolymers, cellulose acetates, polyethylenes, polymethyl methacrylates, polydimethyl-siloxanes, hardened oil, beeswax, carnauba wax, sucrose fatty acid esters, sorbitan monostearate, glyceryl monostearate, glyceryl monomyristate, glyceryl distearate, stearic acid, stearyl alcohol, and mixtures thereof.

7. A method according to claim 6, wherein arotinolol hydrochloride is used as the basic medical agent hydrochloride.

8. A method according to claim 6, wherein the slightly water-soluble substance is an ethyl cellulose, a hydroxypropylmethyl cellulose acetate succinate, an aminoalkylmethacrylate copolymer, a methacrylic acid copolymer, or a mixture thereof.

9. A method according to claim 6, which further comprises the step of:
   packing the coated granules into hard gelatin capsules or tableting the coated granules, together with a pharmaceutically acceptable additive particle or a particulate matter comprising a pharmaceutically acceptable additive.

10. A method according to claim 6, which further comprises the step of:
    packing the coated granules into hard gelatin capsules or tableting the coated granules, together with pharmaceutically acceptable additive particles or a particulate matter comprising a pharmaceutically acceptable additive which contains the same basic medical agent hydrochloride as in the coated granules.

11. A sustained-release preparation according to claim 1, wherein the basic medical agent hydrochloride is arotinolol hydrochloride.

12. A sustained-release preparation according to claim 1, wherein the slightly water-soluble macromolecular substance is selected from an ethyl cellulose, a hydroxypropylmethyl cellulose acetate succinate, an aminoalkylmethacrylate copolymer, a methacrylic acid copolymer, and a mixture thereof.

13. A sustained-release preparation according to claim 1, wherein the basic medical agent hydrochloride is arotinolol hydrochloride, the polyanion having a carboxy group in the side chain is carboxymethyl cellulose calcium, and the slightly water-soluble macromolecular substance is ethyl cellulose.

14. A sustained-release preparation according to claim 1, wherein the basic medical agent hydrochloride is arotinolol hydrochloride, the polyanion having a carboxy group in the side chain is carboxyvinyl polymer, and the slightly water-soluble macromolecular substance is ethyl cellulose.

* * * * *